US007982097B2

(12) United States Patent
Ruezinsky et al.

(10) Patent No.: US 7,982,097 B2
(45) Date of Patent: *Jul. 19, 2011

(54) PROMOTER MOLECULES FOR USE IN PLANTS

(75) Inventors: Diane M. Ruezinsky, Grover, MO (US); Deborah J. Hawkins, Davis, CA (US); Santiago Navarro, St. Louis, MO (US); Laurence D. Parnell, Cambridge, MA (US)

(73) Assignee: Monsanto Technology LLC, St. Louis, MO (US)

( * ) Notice: Subject to any disclaimer, the term of this patent is extended or adjusted under 35 U.S.C. 154(b) by 385 days.

This patent is subject to a terminal disclaimer.

(21) Appl. No.: 11/961,927

(22) Filed: Dec. 20, 2007

(65) Prior Publication Data

US 2008/0241340 A1    Oct. 2, 2008

Related U.S. Application Data

(63) Continuation of application No. 11/224,322, filed on Sep. 12, 2005, now Pat. No. 7,417,177.

(60) Provisional application No. 60/609,535, filed on Sep. 13, 2004.

(51) Int. Cl.
*C12N 15/82* (2006.01)
*A01H 5/00* (2006.01)
*A01H 5/10* (2006.01)

(52) U.S. Cl. ..... 800/287; 800/298; 536/24.1; 435/320.1; 435/419; 435/468

(58) Field of Classification Search .................. None
See application file for complete search history.

(56) References Cited

U.S. PATENT DOCUMENTS

| 5,391,725 | A | 2/1995 | Coruzzi et al. | 800/300 |
|---|---|---|---|---|
| 5,428,147 | A | 6/1995 | Barker et al. | 536/24.1 |
| 5,447,858 | A | 9/1995 | Key et al. | 435/6 |
| 5,589,583 | A | 12/1996 | Klee et al. | 800/298 |
| 5,608,144 | A | 3/1997 | Baden et al. | 800/287 |
| 5,614,399 | A | 3/1997 | Quail et al. | 435/424 |
| 5,633,435 | A | 5/1997 | Barry et al. | 800/288 |
| 5,633,441 | A | 5/1997 | De Greef et al. | 800/271 |
| 5,898,096 | A | 4/1999 | Klee et al. | 800/298 |
| 6,096,950 | A | 8/2000 | John | 800/314 |
| 6,100,077 | A | 8/2000 | Sturley et al. | 435/193 |
| 6,194,636 | B1 | 2/2001 | McElroy et al. | 800/278 |
| 6,232,526 | B1 | 5/2001 | McElroy et al. | 800/278 |
| 6,344,548 | B1 | 2/2002 | Farese, Jr. et al. | 536/23.2 |
| 6,444,876 | B1 | 9/2002 | Lassner et al. | 800/281 |
| 6,448,387 | B1 | 9/2002 | Slater et al. | 536/23.1 |
| 6,476,295 | B2 * | 11/2002 | Barry et al. | 800/284 |
| 6,506,565 | B1 | 1/2003 | Conner et al. | 435/6 |
| 6,822,141 | B2 | 11/2004 | Lardizabal et al. | 800/281 |
| 7,294,711 | B2 | 11/2007 | Ruezinsky et al. | 800/278 |
| 7,417,177 | B2 * | 8/2008 | Ruezinsky et al. | 800/287 |
| 7,511,189 | B2 | 3/2009 | Zou et al. | 800/278 |
| 7,524,945 | B2 | 4/2009 | Cahoon et al. | 800/281 |
| 2003/0028923 | A1 | 2/2003 | Lardizabal et al. | 800/281 |
| 2004/0088759 | A1 * | 5/2004 | Cahoon et al. | 800/281 |
| 2004/0088764 | A1 | 5/2004 | Gleba et al. | 800/278 |
| 2006/0064777 | A1 | 3/2006 | Ruezinsky et al. | 800/281 |
| 2006/0070140 | A1 | 3/2006 | Ruezinsky et al. | 800/281 |

FOREIGN PATENT DOCUMENTS

| EP | 1 033 405 | 9/2000 |
|---|---|---|
| WO | WO 99/63096 | 12/1999 |
| WO | WO 00/36114 | 6/2000 |

OTHER PUBLICATIONS

Delseny et al 1999 GenBank Accession AL133452, see attached alignment.*
Coleman et al., "Physiological and nutritional regulation of enzymes of triacylglycerol synthesis," *Annu. Rev. Nutr.*, 20:77-103, 2000.
Daum et al., "Biochemistry, cell biology and molecular biology of lipids of *Saccharomyces cerevisiae*," *Yeast*, 14:1471-1510, 1998.
Finnlayson et al., "NAD+-specific glycerol 3-phosphate dehydrogenase from developing castor bean endosperm," *Arch. Biochem. Biophys.*, 199:179-185, 1980.
Harwood, "Recent advances in the biosynthesis of plant fatty acids," *Biochem. Biophysics. Acta*, 1301:7-56, 1996.
Hobbs et al., "Cloning of a cDNA encoding diacylglycerol acyltransferase from *Arabidopsis thaliana* and its functional expression," *FEBS Letters*, 452:145-149, 1999.
Kennedy et al., The function of cytidine coenzymes in the biosynthesis of phospholipides, *J. Biol. Chem.*, 222:193, 1956.
Lardizabal et al., "DGAT2 is a new diacylglyceraol gene family—Purification, cloning, and expression in insect cells of two polypeptides from *Mortierella ramanniana* with diacylglycerol acyltransferase activity," *J. Biol. Chem.*, 276:38862-38869, 2001.
Lu and Hills, "Arabidopsis mutants deficient in diacylglycerol acyltransferase display increased sensitivity to abscisic acid, sugars, and osmotic stress during germination and seedling development," *Plant Physiol*, 128:1352-1358, 2002.
Lu et al., "Expression pattern of diacylglycerol acyltransferase-1, an enzyme involved in triacylglycerol biosynthesis, in *Arabidopsis thaliana*," *Plant Mol. Biol.*, 52:31-41, 2003. GenBank Accession No. ATF26013.
Giannoulia et al., "Differential expression of diacylglycerol acyltransferase (DGAT) genes in olive tissues," *Biochem. Soc. Trans.*, 25(6):695-697, 2000.
Zou et al., "The *Arabidopsis thaliana* TAG1 mutant has a mutation in a diacylglycerol acyltransferase gene," *Plant J.*, 52(1):645-653, 1999.
Benfey et al, "The CaMV 35S enhancer contains at least two domains which can confer different developmental and tissue-specific expression patterns," *EMBO J.*, 8(8):2195-2202, 1989.
Boutillier et al., "Ectopic Expression of baby boom triggers a conversion from vegetative to embryonic growth," *Plant Cell*, 14L1737-1749, 2002.

(Continued)

*Primary Examiner* — Brent Page
(74) *Attorney, Agent, or Firm* — SNR Denton US LLP; Erin C. Robert, Esq.

(57) ABSTRACT

The present invention relates to polynucleotide molecules for regulating gene expression in plants. In particular, the invention relates to promoters that are useful for regulating gene expression of heterologous polynucleotide molecules in plants. The invention also relates to expression constructs and transgenic plants containing the heterologous polynucleotide molecules.

19 Claims, 2 Drawing Sheets

OTHER PUBLICATIONS

Cho et al., "Regulation of root hair initiation and expansin gene expression in arabidopsis," *The Plant Cell*, 14:3237-3253, 2002.

GenBank Accession No. AC005917, dated Feb. 27, 2002.

Kim et al., "A 20 nucleotide upstream element is essential for the nopaline synthase (nos) promoter activity," *Plant Molecular Biology*, 24(1):105-117, 1994.

Odell et al., "Identification of DNA sequences required for activity of the cauliflower mosaic virus 35S promoter," *Nature*, 313:810-812, 1985.

Piechulla et al., "Identification of tomato Lhc promoter regions necessary for circadian expression," *Plant Molecular Biology*, 38:655-662, 1998.

Welch et al., "Structural and functional characterization of the phytoene synthase promoter from *Arabidopsis thaliana*," *Planta*, 216:523-534, 2003.

Ye et al., "Engineering the provitamin A (beta-carotene) biosynthetic pathway into (carotenoid-free) rice endosperm," *Science*, 287(5451):303-305, 2000.

Reissue Application Declaration by Assignee for U.S. Appl. No. 12/648,826, dated Dec. 29, 2009.

Claim Amendment regarding U.S. Patent No. 7,417,177 filed in support of Application for Reissue in U.S. Appl. No. 12/648,826, dated Dec. 29, 2009.

Office Action regarding U.S. Appl. No. 12/648,826, dated Jun. 14, 2010.

Response to Office Action regarding U.S. Appl. No. 12/648,826, dated Sep. 14, 2010.

Reissue Application Declaration by Assignee for U.S. Appl. No. 12/648,826, dated Sep. 14, 2010.

U.S. Appl. No. 12/648,826, filed Dec. 29, 2009, Ruezinsky et al.

Notice of Allowance regarding U.S. Appl. No. 12/648,826, dated Jan. 24, 2011.

Telephonic Interview Summary; Amendment and Response to Office Action regarding U.S. Appl. No. 12/648,826, dated Jan. 10, 2011.

Reissue Application Declaration by Assignee for U.S. Appl. No. 12/648,826, dated Jan. 10, 2011.

Reissue Application Declaration by Assignee for U.S. Appl. No. 12/648,826, dated Mar. 2, 2011.

\* cited by examiner

PROMOTER MOLECULES FOR USE IN PLANTS

The present application is a continuation of U.S. application Ser. No. 11/224,322, filed Sep. 12, 2005 now U.S. Pat. No. 7,417,177, which claims the priority of U.S. Provisional Appl. Ser. No. 60/609,535, filed Sep. 13, 2004, the disclosures of which are incorporated herein by reference in its entirety.

BACKGROUND OF THE INVENTION

1. Field of the Invention

The invention relates to the field of plant molecular biology and more specifically relates to polynucleotide molecules useful for the expression of transgenes in plants. The invention in particular relates to P-Dgat1 and P-Dgat2 promoters isolated from *Arabidopsis thaliana* and useful for expression of transgenes of agronomic importance in seeds of crop plants.

2. Background of the Invention

One of the goals of plant genetic engineering is to produce plants with agronomically desirable characteristics or traits. Advances in genetic engineering have provided the requisite tools to transform plants to contain and express foreign genes. The technological advances in plant transformation and regeneration have enabled researchers to take an exogenous polynucleotide molecule, such as a gene from a heterologous or native source, and incorporate that polynucleotide molecule into a plant genome. The gene can then be expressed in a plant cell to exhibit the added characteristic or trait. In one approach, expression of a gene in a plant cell or a plant tissue that does not normally express such a gene may confer a desirable phenotypic effect. In another approach, transcription of a gene or part of a gene in an antisense orientation may produce a desirable effect by preventing or inhibiting expression of an endogenous gene.

Promoters are polynucleotide molecules that comprise the 5' regulatory elements, which play an integral part in the overall expression of genes in living cells. Isolated promoters that function in plants are useful for modifying plant phenotypes through the methods of genetic engineering. The first step in the process to produce a transgenic plant includes the assembly of various genetic elements into a polynucleotide construct. The construct includes a transcribable polynucleotide molecule (gene of interest) that confers a desirable phenotype when expressed (transcribed) in the plant cells by a promoter that is operably linked to the gene of interest. A promoter in a construct may be homologous or heterologous to the gene of interest also contained therein. The construct is then introduced into a plant cell by various methods of plant transformation to produce a transformed plant cell and the transformed plant cell is regenerated into a transgenic plant. The promoter controls expression of the gene of interest to which the promoter is operably linked and thus affects the characteristic or trait conferred by the expression of the transgene in plants.

For production of transgenic plants with various desired characteristics, it would be advantageous to have a variety of promoters to provide gene expression such that a gene is transcribed efficiently in the amount necessary to produce the desired effect. The commercial development of genetically improved germplasm has also advanced to the stage of introducing multiple traits into crop plants, often referred to as a gene stacking approach. In this approach, multiple genes conferring different characteristics of interest can be introduced into a plant. It is often desired when introducing multiple genes into a plant that each gene is modulated or controlled for optimal expression, leading to a requirement for diverse regulatory elements. In light of these and other considerations, it is apparent that optimal control of gene expression and regulatory element diversity are important in plant biotechnology.

A variety of different types or classes of promoters can be used for plant genetic engineering. Promoters can be classified on the basis of characteristics such as temporal or developmental range, levels of transgene expression, or tissue specificity. For example, promoters referred to as constitutive promoters are capable of transcribing operably linked genes efficiently and expressing those genes in multiple tissues. Different types of promoters can be obtained by isolating the upstream 5' regulatory regions of genes that are transcribed and expressed in the desired manner, e.g., constitutive, tissue enhanced, or developmentally induced.

Numerous promoters, which are active in plant cells, have been described in the literature. These include the nopaline synthase (nos) promoter and octopine synthase (ocs) promoters carried on tumor-inducing plasmids of *Agrobacterium tumefaciens* and the caulimovirus promoters such as the Cauliflower Mosaic Virus (CaMV) 19S or 35S promoter (U.S. Pat. No. 5,352,605), CaMV 35S promoter with a duplicated enhancer (U.S. Pat. Nos. 5,164,316; 5,196,525; 5,322,938; 5,359,142; and 5,424,200), and the Figwort Mosaic Virus (FMV) 35S promoter (U.S. Pat. No. 5,378,619). These promoters and numerous others have been used in the creation of constructs for transgene expression in plants. Other useful promoters are described, for example, in U.S. Pat. Nos. 5,391,725; 5,428,147; 5,447,858; 5,608,144; 5,614,399; 5,633,441; 6,232,526; and 5,633,435, all of which are incorporated herein by reference.

Promoters are also needed for expression of genes in seeds for the production of plant oils and other traits. Diacylglycerol acyltransferase (referred to hereinafter as Dgat) is an integral membrane protein that catalyzes the final enzymatic step in the production of triacylglycerols in plants, fungi, and marnrnals (Harwood, *Biochem. Biophysics. Acta*, 13017-13056 (1996); Daum et al., *Yeast*, 16:1471-1510 (1998); and Coleman et al., *Annu. Rev. Nutr.*, 20:77-103 (2000). Dgat is responsible for transferring an acyl group from acyl-coenzyme-A to 1,2-diacylglycerol (Dag) to form triacylglycerol (TAG). Nearly all commercially important fats and oils of plant origin consist of triacylglycerols. Triacylglycerols are hereafter referred to as "oils" or "plant oils." In plants, particularly in oilseeds, Dgat is associated with the membrane and lipid body fractions, and plays a key role in oil synthesis (Kennedy et al., *J. Biol. Chem.*, 222:193 (1956); Finnlayson et al., *Arch. Biochem. Biophys.*, 199:179-185 (1980)).

Two different families of Dgat proteins have been identified. The first family of Dgat proteins (referred to hereinafter as Dgat1) is related to the acyl-coenzyme A:cholesterol acyltransferase (ACAT) and has been described in the literature (see, e.g., U.S. Pat. Nos. 6,100,077 and 6,344,548). A second family of Dgat proteins (referred to hereinafter as Dgat2), unrelated to the previously identified family of Dgat1 proteins, is described in U.S. Published Application US20030028923. The present invention describes promoters associated with these Dgat families.

While previous work has provided a number of promoters useful to direct transcription in transgenic plants, there is still a need for novel promoters with beneficial expression characteristics. In particular, there is a need for promoters that are capable of directing expression of exogenous genes, for oil production, in seeds. Many previously identified promoters fail to provide the patterns or levels of expression required to fully realize the benefits of expression of selected seed-enhanced oil-associated genes in transgenic plants. There is, therefore, a need in the art of plant genetic engineering for novel promoters for use in oilseeds.

SUMMARY OF THE INVENTION

The present invention provides genetic tools that answer the need of both altering the composition of oils produced in a plant as well as the percentage content thereof relative to other components of a seed, including, for example, the meal content thereof. The present invention includes diacylglycerol acyltransferase (Dgat) promoters, which can be used to direct the transcription of genes involved in the production in seeds of agronomic traits such as increased oil, starch and protein.

In one embodiment, the present invention provides a promoter comprising a polynucleotide sequence substantially homologous to a polynucleotide sequence selected from the group consisting of SEQ ID NO:1 and SEQ ID NO:4, and fragments thereof that are capable of regulating transcription of operably linked polynucleotide molecules. Also provided by the invention are polynucleotide sequences comprising at least about 70% sequence identity to any of these sequences, including sequences with about 75%, 80%, 83%, 85%, 88%, 90%, 92%, 94%, 95%, 96%, 98%, 99% or more sequence identity to any one or more of SEQ ID NO:1 or SEQ ID NO:4 or a fragment thereof capable of regulating transcription of operably linked polynucleotide molecules, e.g., having promoter activity. In particular embodiments, a fragment of a sequence provided herein is defined as comprising at least about 30, 40, 50, 75, 100, 125, 150, 200, 250, 300, 350, 400, 450, 500, 600, 750, 900, 1000, or more contiguous nucleotides of any of the promoter sequences described herein, including, for example, SEQ ID NO:1 and SEQ ID NO:4.

In another embodiment, the invention provides a plant expression construct comprising a promoter sequence described herein, for example, comprising a polynucleotide sequence substantially homologous to a polynucleotide sequence selected from the group consisting of SEQ ID NOs:1 and 4 or any fragments thereof, wherein said promoter is operably linked to a transcribable polynucleotide molecule and may also be operably linked to a 3' transcription termination polynucleotide molecule.

In yet another embodiment, the invention provides a transgenic plant stably transformed with a plant expression construct provided by the invention. In one embodiment, the construct comprises a promoter comprising a polynucleotide sequence substantially homologous to a polynucleotide sequence selected from the group consisting of SEQ ID NOs:1 and 4 or any fragments or regions thereof, wherein said promoter is operably linked to a transcribable polynucleotide molecule, and optionally, operably linked to a 3' transcription termination polynucleotide molecule.

In another embodiment, the invention provides a method of making a vegetable oil, comprising obtaining a transgenic plant provided by the invention, for example, by incorporating into the genome of an oilseed plant a promoter of the present invention operably linked to a transcribable polynucleotide molecule conferring altered oil and/or protein content, and extracting oil and/or protein from the seeds and/or other plant parts. In one aspect, the plant may be defined as an oilseed plant. The method may comprise growing the plant to produce protein and/or oil. The invention also provides methods for producing food and feed from a plant provided herein.

In one aspect, this involves obtaining a plant or part thereof provided by the invention and preparing food or feed therefrom.

In one aspect, the invention provides a method of making a vegetable oil comprising incorporating into the genome of an oilseed plant a promoter of the present invention operably linked to a transcribable polynucleotide molecule encoding an oil enhancing gene, which confers altered oil content, for example, Diacylglycerol Acyltransferase (Dgat, EC 2.3.1.20, U.S. Pat. No. 6,444,876), Phosphatidic Acid Phosphatase (Pap, EC 3.1.3.4, U.S. Pat. Nos. 6,495,739 and 6,476,294), and Leucoanthocyanidin Dioxygenase (Dox, EC 1.14.11, WO 04/046336). The method may comprise growing the oilseed plant to produce oilseeds, and extracting the oil and/or protein from the oilseed.

In another embodiment, a food or feed prepared by the invention is a commodity food or feed product, such as vegetable starch. The invention this provides a method comprising incorporating into the genome of an oilseed plant a promoter of the present invention (SEQ ID NO: 1 and 4) operably linked to a transcribable polynucleotide molecule encoding a starch enhancing gene, which confers increased starch content, comprising Sucrose Phosphorylase (Sm.gtfA, EC 2.4.1.7, U.S. Pat. No. 6,235,971), growing the oilseed plant to produce starch enriched seeds, and extracting the starch and/or protein from the oilseed.

In another embodiment, the invention provides a method of altering cell proliferation, comprising the steps of incorporating into the genome of an oilseed plant a promoter of the present invention (SEQ ID NO: 1 and 4) operably linked to a transcribable polynucleotide molecule encoding a cell proliferation gene.

The foregoing and other aspects of the invention will become more apparent from the following detailed description and accompanying drawings.

BRIEF DESCRIPTION OF THE SEQUENCES

SEQ ID NO: 1 sets forth a polynucleotide sequence of a P-Dgat1 promoter.
SEQ ID NO: 2 sets forth a P-Dgat1 primer sequence.
SEQ ID NO: 3 sets forth a P-Dgat1 primer sequence.
SEQ ID NO: 4 sets forth a polynucleotide sequence of a P-Dgat2 promoter.
SEQ ID NO: 5 sets forth a P-Dgat2 primer sequence.
SEQ ID NO: 6 sets forth a P-Dgat2 primer sequence.

DETAILED DESCRIPTION OF THE INVENTION

The following definitions and methods are provided to better define the present invention and to guide those of ordinary skill in the art in the practice of the present invention. Unless otherwise noted, terms are to be understood according to conventional usage by those of ordinary skill in the relevant art.

As used herein, the phrase "polynucleotide molecule" refers to the single- or double-stranded DNA or RNA of genomic or synthetic origin, i.e., a polymer of deoxyribonucleotide or ribonucleotide bases, respectively, read from the 5' (upstream) end to the 3' (downstream) end.

As used herein, the phrase "polynucleotide sequence" refers to the sequence of a polynucleotide molecule. The nomenclature for DNA bases as set forth at 37 CFR §1.822 is used.

Promoters

As used herein, the term "promoter" refers to a polynucleotide molecule that in its native state is located upstream or 5' to a translational start codon of an open reading frame (or protein-coding region) and that is involved in recognition and binding of RNA polymerase II and other proteins (trans-acting transcription factors) to initiate transcription. A "plant promoter" is a native or non-native promoter that is functional in plant cells. Constitutive plant promoters are functional in most or all tissues of a plant throughout plant development. Any plant promoter can be used as a 5' regulatory element for modulating expression of a particular gene or genes operably associated thereto. When operably linked to a transcribable polynucleotide molecule, a promoter typically causes the transcribable polynucleotide molecule to be transcribed in a manner that is similar to that of which the promoter is normally associated. Plant promoters can include promoters produced through the manipulation of known promoters to produce artificial, chimeric, or hybrid promoters. Such promoters can also combine cis-elements from one or more promoters, for example, by adding a heterologous regulatory element to an active promoter with its own partial or complete regulatory elements. Thus, the design, construction, and use of chimeric or hybrid promoters comprising at least one cis-element of SEQ ID NOs: 1 and 4 for modulating the expression of operably linked polynucleotide sequences is encompassed by the present invention.

As used herein, the term "cis-element" refers to a cis-acting transcriptional regulatory element that confers an aspect of the overall control of gene expression. A cis-element may function to bind transcription factors, trans-acting protein factors that regulate transcription. Some cis-elements bind more than one transcription factor, and transcription factors may interact with different affinities with more than one cis-element. The promoters of the present invention desirably contain cis-elements that can confer or modulate gene expression. Cis-elements can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis with known cis-element motifs by conventional DNA sequence comparison methods. The fine structure of a cis-element can be further studied by mutagenesis (or substitution) of one or more nucleotides or by other conventional methods. Cis-elements can be obtained by chemical synthesis or by isolation from promoters that include such elements, and they can be synthesized with additional flanking nucleotides that contain useful restriction enzyme sites to facilitate subsequence manipulation.

In one embodiment, the promoters of the present invention comprise multiple cis-elements each of which confers a different aspect to the overall control of gene expression. In a preferred embodiment, cis-elements from the polynucleotide molecules of SEQ ID NOs: 1 and 4 are identified using computer programs designed specifically to identify cis-element, domains, or motifs within sequences. Cis-elements may either positively or negatively regulate gene expression, depending on the conditions. The present invention therefore encompasses cis-elements of the disclosed promoters.

As used herein, the phrase "substantially homologous" refers to polynucleotide molecules that generally demonstrate a substantial percent sequence identity with the promoters provided herein. Of particular interest are polynucleotide molecules wherein the polynucleotide molecules function in plants to direct transcription and have at least about 70% sequence identity, at least about 75% sequence identity, at least about 80% sequence identity, at least about 85% sequence identity, and at least about 90% or more sequence identity, including at least about 92%, 95%, 96%, 98% or 99% sequence identity with the polynucleotide sequences of the promoters described herein. Polynucleotide molecules that are capable of regulating transcription of operably linked transcribable polynucleotide molecules and are substantially homologous to the polynucleotide sequences of the promoters provided herein are encompassed within the scope of this invention.

As used herein, the phrase "percent sequence identity" refers to the percentage of identical nucleotides in a linear polynucleotide sequence of a reference polynucleotide molecule (or its complementary strand) as compared to a test polynucleotide molecule (or its complementary strand) when the two sequences are optimally aligned (with appropriate nucleotide insertions, deletions, or gaps totaling less than 20% of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc., San Diego, Calif.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction times 100. The comparison of one or more polynucleotide sequences may be to a full-length polynucleotide sequence or a portion thereof, or to a longer polynucleotide sequence.

As used herein, the term "homology" refers to the level of similarity or percent identity between polynucleotide sequences in terms of percent nucleotide positional identity, i.e., sequence similarity or identity. As used herein, the term homology also refers to the concept of similar functional properties among different polynucleotide molecules, e.g., promoters that have similar function may have homologous cis-elements. Polynucleotide molecules are homologous when under certain conditions they specifically hybridize to form a duplex molecule. Under these conditions, referred to as stringency conditions, one polynucleotide molecule can be used as a probe or primer to identify other polynucleotide molecules that share homology. The phrase "stringent conditions" is functionally defined with regard to the hybridization of a nucleic-acid probe to a target nucleic acid (i.e., to a particular nucleic-acid sequence of interest) by the specific hybridization procedure discussed in *Molecular Cloning: A Laboratory Manual*, $3^{rd}$ edition Volumes 1, 2, and 3. J. F. Sambrook, D. W. Russell, and N. Irwin, Cold Spring Harbor Laboratory Press, 2000 (referred to herein as Sambrook, et al.). Accordingly, the nucleotide sequences of the invention may be used for their ability to selectively form duplex molecules with complementary stretches of polynucleotide molecule fragments. Depending on the application envisioned one would desire to employ varying conditions of hybridization to achieve varying degrees of selectivity of probe towards target sequence. For applications requiring high selectivity, one will typically desire to employ relatively high stringent conditions to form the hybrids, e.g., one will select relatively low salt and/or high temperature conditions, such as provided by about 0.02 M to about 0.15 M NaCl at temperatures of about 50° C. to about 70° C. A high stringent condition, for example, is to wash the hybridization filter at least twice with high-stringency wash buffer (0.2×SSC, 0.1% SDS, 65° C.). Appropriate moderate stringency conditions that promote DNA hybridization, for example, 6.0× sodium chloride/sodium citrate (SSC) at about 45° C., followed by a wash of 2.0×SSC at 50° C., are known to those skilled in the art. Additionally, the salt concentration in the wash step can be selected from a low stringency of about 2.0×SSC at 50° C. to a high stringency of about 0.2×SSC at 50° C. Additionally, the temperature in the wash step can be increased from low stringency conditions at room temperature, about 22° C., to high stringency conditions at about 65° C. Both temperature and salt may be varied, or either the temperature or the salt concentration may be held constant while the other variable is changed. Such selective conditions tolerate little mismatch between the probe and the template or target strand. Detection of polynucleotide molecules via hybridization is well known to those of skill in the art, and the teachings of U.S. Pat. Nos. 4,965,188 and 5,176,995 are exemplary of the methods of hybridization analyses.

Homology can also be determined by computer programs that align polynucleotide sequences and estimate the ability of polynucleotide molecules to form duplex molecules under certain stringency conditions. Polynucleotide molecules from different sources that share a high degree of homology are referred to as "homologues."

Methods well known to one skilled in the art may be used to identify promoters of interest having activity similar to the promoters described herein. For example, cDNA libraries may be constructed using cells or tissues of interest and screened to identify genes having an expression pattern similar to that of the promoters described herein. The cDNA sequence for the identified gene may then be used to isolate the gene's promoter for further characterization. See, for example U.S. Pat. Nos. 6,096,950; 5,589,583; and 5,898,096, incorporated herein by reference. Alternately, transcriptional profiling or electronic northern techniques may be used to identify genes having an expression pattern similar to that of the promoters described herein. Once these genes have been identified, their promoters may be isolated for further characterization. See, for example U.S. Pat. Nos. 6,506,565 and 6,448,387, incorporated herein by reference. The electronic northern technique refers to a computer-based sequence analysis which allows sequences from multiple cDNA libraries to be compared electronically based on parameters the researcher identifies including abundance in EST populations in multiple cDNA libraries, or exclusively to EST sets from one or combinations of libraries. The transcriptional profiling technique is a high-throughput method used for the systematic monitoring of gene expression profiles for thousands of genes. This DNA chip-based technology arrays thousands of cDNA sequences on a support surface. These arrays are simultaneously hybridized to a population of labeled cDNA probes prepared from RNA samples of different cell or tissue types, allowing direct comparative analysis of expression. This approach may be used for the isolation of regulatory sequences such as promoters associated with those genes.

In another embodiment, the promoter disclosed herein can be modified. Those skilled in the art can create promoters that have variations in the polynucleotide sequence. The polynucleotide sequences of the promoters of the present invention as shown in SEQ ID NOs: 1 and 4 may be modified or altered to enhance their control characteristics. One preferred method of alteration of a polynucleotide sequence is to use PCR to modify selected nucleotides or regions of sequences. These methods are well known to those of skill in the art. Sequences can be modified, for example by insertion, deletion, or replacement of template sequences in a PCR-based DNA modification approach. A "variant" is a promoter containing changes in which one or more nucleotides of an original promoter is deleted, added, and/or substituted, preferably while substantially maintaining promoter function. For example, one or more base pairs may be deleted from the 5' or 3' end of a promoter to produce a "truncated" promoter. One or more base pairs can also be inserted, deleted, or substituted internally to a promoter. In the case of a promoter fragment, variant promoters can include changes affecting the transcription of a minimal promoter to which it is operably linked. A minimal or basal promoter is a polynucleotide molecule that is capable of recruiting and binding the basal transcription machinery. One example of basal transcription machinery in eukaryotic cells is the RNA polymerase II complex and its accessory proteins. Variant promoters can be produced, for example, by standard DNA mutagenesis techniques or by chemically synthesizing the variant promoter or a portion thereof.

Novel chimeric promoters can be designed or engineered by a number of methods. Many promoters contain cis-elements that activate, enhance, or define the strength and/or specificity of the promoter. For example promoters may contain "TATA" boxes defining the site of transcription initiation and other cis-elements located upstream of the transcription initiation site that modulate transcription levels. For example, a chimeric promoter may be produced by fusing a first promoter fragment containing the activator cis-element from one promoter to a second promoter fragment containing the activator cis-element from another promoter; the resultant chimeric promoter may cause an increase in expression of an operably linked transcribable polynucleotide molecule. Promoters can be constructed such that promoter fragments or elements are operably linked, for example, by placing such a fragment upstream of a minimal promoter. The cis-elements and fragments of the present invention can be used for the construction of such chimeric promoters. Methods for construction of chimeric and variant promoters of the present invention include, but are not limited to, combining control elements of different promoters or duplicating portions or regions of a promoter (see, for example, U.S. Pat. Nos. 4,990,607; 5,110,732; and 5,097,025, all of which are herein incorporated by reference). Those of skill in the art are familiar with the standard resource materials that describe specific conditions and procedures for the construction, manipulation, and isolation of macromolecules (e.g., polynucleotide molecules, plasmids, etc.), as well as the generation of recombinant organisms and the screening and isolation of polynucleotide molecules.

In another embodiment, a promoter comprising the polynucleotide sequence shown in SEQ ID NOs: 1 and 4 includes any length of said polynucleotide sequence that is capable of regulating an operably linked transcribable polynucleotide molecule. For example, the promoters as disclosed in SEQ ID NOs: 1 and 4 may be truncated or portions may be deleted while still retaining the capacity to regulate transcription of an operably linked polynucleotide molecule. In a related embodiment, a cis-element of the disclosed promoters may confer a particular specificity such as conferring enhanced expression of operably linked polynucleotide molecules in certain tissues and therefore is also capable of regulating transcription of operably linked polynucleotide molecules. Consequently, any fragments, portions, or regions of the promoters comprising the polynucleotide sequence shown in SEQ ID NOs: 1 and 4 can be used as regulatory polynucleotide molecules, including but not limited to cis-elements or motifs of the disclosed polynucleotide molecules. Substitutions, deletions, insertions, or any combination thereof can be combined to produce a final construct.

Polynucleotide Constructs

As used herein, the term "construct" refers to any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner.

As used herein, the phrase "operably linked" refers to a first polynucleotide molecule, such as a promoter, connected with a second transcribable polynucleotide molecule, such as a gene of interest, where the polynucleotide molecules are so arranged that the first polynucleotide molecule affects the function of the second polynucleotide molecule. Preferably, the two polynucleotide molecules are part of a single contiguous polynucleotide molecule and more preferably are adjacent. For example, a promoter is operably linked to a gene of interest if the promoter regulates or mediates transcription of the gene of interest in a cell.

As used herein, the phrase "transcribable polynucleotide molecule" refers to any polynucleotide molecule capable of being transcribed into a RNA molecule. Methods are known for introducing constructs into a cell in such a manner that the transcribable polynucleotide molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present invention, conventional compositions and methods for preparing and using constructs and host cells are well known to one skilled in the art (see, for example, Sambrook, et al.).

Constructs of the present invention may contain a promoter operably linked to a transcribable polynucleotide molecule operably linked to a 3' transcription termination polynucleotide molecule. In addition, constructs may include but are not limited to additional regulatory polynucleotide molecules from the 3'-untranslated region (3' UTR) of plant genes (e.g., a 3' UTR to increase mRNA stability of the mRNA, such as the PI-II termination region of potato or the octopine or nopaline synthase 3' termination regions). Constructs may include but are not limited to the 5' untranslated regions (5' UTR) of an mRNA polynucleotide molecule which can play an important role in translation initiation and can also be a genetic component in a plant expression construct. For example, non-translated 5' leader polynucleotide molecules derived from heat shock protein genes have been demonstrated to enhance gene expression in plants (see, for example, U.S. Pat. Nos. 5,659,122 and 5,362,865; and U.S. Published Application No. 2002/0192812, herein incorporated by reference). These additional upstream and downstream regulatory polynucleotide molecules may be derived from a source that is native or heterologous with respect to the other elements present on the promoter construct.

Thus, constructs of the present invention comprise promoters such as those provided in SEQ ID NOs: 1 and 4 or modified as described above, operatively linked to a transcribable polynucleotide molecule so as to direct transcription of said transcribable polynucleotide molecule at a desired level or in a desired tissue or developmental pattern upon introduction of said construct into a plant cell. In some cases, the transcribable polynucleotide molecule comprises a protein-coding region of a gene, and the promoter provides for transcription of a functional mRNA molecule that is translated and expressed as a protein product. Constructs may also be constructed for transcription of antisense RNA molecules or other similar inhibitory RNA in order to inhibit expression of a specific RNA molecule of interest in a target host cell.

Exemplary transcribable polynucleotide molecules for incorporation into constructs of the present invention include, for example, DNA molecules or genes from a species other than the target gene species, or even genes that originate with or are present in the same species, but are incorporated into recipient cells by genetic engineering methods rather than classical reproduction or breeding techniques. Exogenous gene or genetic element is intended to refer to any gene or DNA molecule that is introduced into a recipient cell. The type of DNA included in the exogenous DNA can include DNA that is already present in the plant cell, DNA from another plant, DNA from a different organism, or a DNA generated externally, such as a DNA molecule containing an antisense message of a gene, or a DNA molecule encoding an artificial or modified version of a gene.

The promoters of the present invention can be incorporated into a construct using marker genes as described and tested in transient analyses that provide an indication of gene expression in stable plant systems. As used herein the phrase "marker gene" refers to any transcribable polynucleotide molecule whose expression can be screened for or scored in some way. Methods of testing for marker gene expression in transient assays are known to those of skill in the art. Transient expression of marker genes has been reported using a variety of plants, tissues, and DNA delivery systems. For example, types of transient analyses can include but are not limited to direct gene delivery via electroporation or particle bombardment of tissues in any transient plant assay using any plant species of interest. Such transient systems would include but are not limited to electroporation of protoplasts from a variety of tissue sources or particle bombardment of specific tissues of interest. The present invention encompasses the use of any transient expression system to evaluate promoters or promoter fragments operably linked to any transcribable polynucleotide molecules, including but not limited to selected reporter genes, marker genes, or genes of agronomic interest. Examples of plant tissues envisioned to test in transients via an appropriate delivery system would include but are not limited to leaf base tissues, callus, cotyledons, roots, endosperm, embryos, floral tissue, pollen, and epidermal tissue.

Any scorable or screenable marker gene can be used in a transient assay. Preferred marker genes for transient analyses of the promoters or promoter fragments of the present invention include a GUS gene (U.S. Pat. No. 5,599,670, herein incorporated by reference) or a GFP gene (U.S. Pat. No. 5,491,084, herein incorporated by reference). The constructs containing the promoters or promoter fragments operably linked to a marker gene are delivered to the tissues and the tissues are analyzed by the appropriate mechanism, depending on the marker. The quantitative or qualitative analyses are used as a tool to evaluate the potential expression profile of the promoters or promoter fragments when operatively linked to genes of agronomic interest in stable plants.

Thus, in one preferred embodiment, a polynucleotide molecule of the present invention as shown in SEQ ID NOs: 1 and 4 or fragments, variants, or derivatives thereof is incorporated into a construct such that a promoter of the present invention is operably linked to a transcribable polynucleotide molecule that provides for a selectable, screenable, or scorable marker. Markers for use in the practice of the present invention include, but are not limited to transcribable polynucleotide molecules encoding β-glucuronidase (GUS), green fluorescent protein (GFP), luciferase (LUC), proteins that confer antibiotic resistance, or proteins that confer herbicide tolerance. Useful antibiotic resistance markers, including those encoding proteins conferring resistance to kanamycin (nptII), hygromycin B (aph IV), streptomycin or spectinomycin (aad, spec/strep), and gentamycin (aac3 and aacC4) are known in the art. Herbicides for which transgenic plant tolerance has been demonstrated and the method of the present invention can be applied, include but are not limited to: glyphosate, glufosinate, sulfonylureas, imidazolinones, bromoxynil, delapon, cyclohezanedione, protoporphyrionogen oxidase inhibitors, and isoxasflutole herbicides. Polynucleotide molecules encoding proteins involved in herbicide tolerance are known in the art, and include, but are not limited to a polynucleotide molecule encoding 5-enolpyruvylshikimate-3-phosphate synthase (EPSPS) described in U.S. Pat. Nos. 5,627,061; 5,633,435; and 6,040,497; and aroA described in U.S. Pat. No. 5,094,945 for glyphosate tolerance; a polynucleotide molecule encoding bromoxynil nitrilase (Bxn) described in U.S. Pat. No. 4,810,648 for Bromoxynil tolerance; a polynucleotide molecule encoding phytoene desaturase (crtI) described in Misawa et al., *Plant J*, 4:833-840 (1993) and Misawa et al., *Plant J*, 6:481-489 (1994) for norflurazon tolerance; a polynucleotide molecule encoding acetohydroxyacid synthase (AHAS, aka ALS) described in Sathasiivan et al., *Nucl. Acids Res.*, 18:2188-2193 (1990) for tolerance to sulfonylurea herbicides; and the bar gene described in DeBlock, et al., *EMBO J.*, 6:2513-2519 (1987) for glufosinate and bialaphos tolerance.

In one preferred embodiment, a polynucleotide molecule of the present invention as shown in SEQ ID NOs: 1 and 4 or fragments, variants, or derivatives thereof is incorporated into a construct such that a promoter of the present invention is operably linked to a transcribable polynucleotide molecule that is a gene of agronomic interest. As used herein, the phrase "gene of agronomic interest" refers to a transcribable polynucleotide molecule that includes but is not limited to a gene that provides a desirable characteristic associated with plant morphology, physiology, growth and development, yield, nutritional enhancement, disease or pest resistance, or environmental or chemical tolerance. The expression of a gene of agronomic interest is desirable in order to confer an agronomically important trait. A gene of agronomic interest that provides a beneficial agronomic trait to crop plants may be, for example, including, but not limited to genetic elements comprising herbicide resistance (U.S. Pat. Nos. 5,633,435 and 5,463,175), increased yield (U.S. Pat. No. 5,716,837), insect control (U.S. Pat. Nos. 6,063,597; 6,063,756; 6,093,695; 5,942,664; and 6,110,464), fungal disease resistance (U.S. Pat. Nos. 5,516,671; 5,773,696; 6,121,436; 6,316,407; and 6,506,962), virus resistance (U.S. Pat. Nos. 5,304,730 and 6,013,864), nematode resistance (U.S. Pat. No. 6,228,992), bacterial disease resistance (U.S. Pat. No. 5,516,671), starch production (U.S. Pat. Nos. 5,750,876 and 6,476,295), modified oils production (U.S. Pat. No. 6,444,876), high oil production (U.S. Pat. Nos. 5,608,149 and 6,476,295), modified fatty acid content (U.S. Pat. No. 6,537,750), high protein production (U.S. Pat. No. 6,380,466), fruit ripening (U.S. Pat. No. 5,512,466), enhanced animal and human nutrition (U.S. Pat. Nos. 5,985,605 and 6,171,640), biopolymers (U.S. Pat. No. 5,958,745 and U.S. Published Application No. 2003/0028917), environmental stress resistance (U.S. Pat. No. 6,072,103), pharmaceutical peptides (U.S. Pat. No. 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), and biofuel production (U.S. Pat. No. 5,998,700), the genetic elements and transgenes described in the patents listed above are herein incorporated by reference.

Alternatively, a transcribable polynucleotide molecule can effect the above mentioned phenotypes by encoding a non-translatable RNA molecule that causes the targeted inhibition of expression of an endogenous gene, for example via antisense, RNAi, or cosuppression-mediated mechanisms. The RNA could also be a catalytic RNA molecule (i.e., a ribozyme) engineered to cleave a desired endogenous mRNA product. Thus, any polynucleotide molecule that encodes a protein or mRNA that expresses a phenotype or morphology change of interest is useful for the practice of the present invention.

The constructs of the present invention may comprise double Ti plasmid border DNA constructs that have the right border (RB or AGRtu.RB) and left border (LB or AGRtu.LB) regions of the Ti plasmid isolated from *Agrobacterium tumefaciens* comprising a T-DNA, that along with transfer molecules provided by the *Agrobacterium* cells, permits the integration of the T-DNA into the genome of a plant cell. The constructs may also contain the plasmid backbone DNA segments that provide replication function and antibiotic selection in bacterial cells, for example, an *E. coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *Agrobacterium tumefaciens* ABI, C58, or LBA4404, however, other strains known to those skilled in the art of plant transformation can function in the present invention.

Transformed Plants And Plant Cells

As used herein, the term "transformed" refers to a cell, tissue, organ, or organism into which has been introduced a foreign polynucleotide molecule, such as a construct. Preferably, the introduced polynucleotide molecule is integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic plant as a parent in a cross and exhibiting an altered phenotype resulting from the presence of a foreign polynucleotide molecule. A plant transformation construct containing a promoter of the present invention may be introduced into plants by any plant transformation method. Methods and materials for transforming plants by introducing a plant expression construct into a plant genome in the practice of this invention can include any of the well-known and demonstrated methods including electroporation as illustrated in U.S. Pat. No. 5,384,253; microprojectile bombardment as illustrated in U.S. Pat. Nos. 5,015,580; 5,550,318; 5,538,880; 6,160,208; 6,399,861; and 6,403,865; *Agrobacterium*-mediated transformation as illustrated in U.S. Pat. Nos. 5,635,055; 5,824,877; 5,591,616; 5,981,840; and 6,384,301; and protoplast transformation as illustrated in U.S. Pat. No. 5,508,184, all of which are incorporated herein by reference.

Methods for specifically transforming dicots are well known to those skilled in the art. Transformation and plant regeneration using these methods have been described for a number of crops including, but not limited to, cotton (*Gossypium hirsutum*), soybean (*Glycine max*), peanut (*Arachis hypogaea*), members of the genus *Brassica*; and alfalfa (*Medicago sativa*).

Methods for specifically transforming monocots are well known to those skilled in the art. Transformation and plant regeneration using these methods have been described for a number of crops including, but not limited to, barley (*Hordeum vulgarae*); maize (*Zea mays*); oats (*Avena sativa*); orchard grass (*Dactylis glomerata*); rice (*Oryza sativa*, including indica and japonica varieties); sorghum (*Sorghum bicolor*); sugar cane (*Saccharum* sp); tall fescue (*Festuca arundinacea*); turfgrass (*Agrostis*); wheat (*Triticum aestivum*), millet, and rye.

It is apparent to those of skill in the art that a number of transformation methodologies can be used and modified for production of stable transgenic plants from any number of target crops of interest.

Many seeds, nuts, and kernels contain oil that can be extracted and used in cooking, as an ingredient in other foods, as a nutritional supplement, as a raw material for the manufacture of soap, body and hair oils, detergents, paints, as well as, replacements for certain petroleum-based lubricants and fuels. As used herein, these seeds, nuts, and kernels collectively are termed "oil seeds" (National Sustainable Agriculture Information Service (ATTRA), Fayetteville, Ark.). Table 1 lists examples of seeds, nuts, and kernels commonly classified as oil seeds.

TABLE 1

Oil containing seeds, nuts, kernels

| | | |
|---|---|---|
| Apricot stones | Black currant | Red pepper |
| Avocado | Jojoba | Brazil nut |
| Cotton seed | Coffee | Passion fruit |
| Billberry | Cocoa | Pecan |
| Borage | Coriander | Pistachio |
| Stinging nettle | Caraway seed | Rape seed |
| Beech nut | Pumpkin seed | Castor bean |
| *Calendula* | Linseed | Sea buckthorn |
| Cashew nut | Mace | Mustard seed |
| Copra (dried coconut) | Corn seed | Sesame seed |
| Safflower | *Macadamia* nut | Soybean |
| Groundnut | Almonds | Sunflower seed |
| Spurge | Melon seed | Tropho plant |
| Rubber seed | Poppy | Tomato seed |
| Rose hip | Nutmeg | Grape seed |
| Hemp | Evening primrose | Walnut |
| Hazelnut | Neem seed | Citrus seed |
| Raspberry | Niger seed | Canola |
| Elderberry | Palm kernel | |

In another embodiment, the invention provides a method of making a vegetable oil, comprising the steps of incorporating into the genome of an oilseed plant a promoter of the present invention operably linked to a transcribable polynucleotide molecule conferring altered oil and/or protein content, growing the oilseed plant to produce oilseeds, and extracting the oil and/or protein from the oilseed.

The transformed plants are analyzed for the presence of the genes of interest and the expression level and/or profile conferred by the promoters of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays.

The seeds of this invention can be harvested from fertile transgenic plants and be used to grow progeny generations of transformed plants of this invention including hybrid plant lines comprising the construct of this invention and expressing a gene of agronomic interest. The terms "seeds" and "kernels" are understood to be equivalent in meaning. The term kernel is frequently used in describing the seed of a corn or rice plant. In all plants the seed is the mature ovule consisting of a seed coat, embryo, aleurone, and an endosperm.

The promoter of the present invention provides for differential expression in plant tissues, preferably in at least one plant seed tissue that includes seed coat, embryo, aleurone, and endosperm. The promoters are herein referred to as "seed enhanced promoters."

The present invention relates to altering the cell cycle in plants through the manipulation of the expression of cell proliferation genes in the seed to alter the number of cells and size of seed-specific organs such as the embryo and/or aleurone. Larger seed-specific organs result in more oil, micronutrients, protein, or starch produced per seed. Various strategies to modify the cell cycle are encompassed by the present invention.

The phrase "cell proliferation" refers to cells undergoing mitotic cell divisions, such as in rapidly growing tissues. Cell proliferation can be enhanced by expression of genes involved in the cell proliferation process, including but not restricted to, CYCD2; 1 (CYCD2) and CYCD3; 1 (CYCD3) (GenBank accessions X83370 and X83371, Soni et al., *Plant Cell*, 7:85-103 (1995)), E2Fb (GenBank accession AJ294533, Richard et al., *Plant Cell, Tissue and Organ Culture*, 69: 167-176 (2002)), AINTEGUMENTA (GenBank accession U41339, Elliott et al., Plant Cell, 8 (2): 155-168 (1996)).

In a similar manner, cell proliferation can be interrupted or inhibited by expression of genes involved in cell proliferation including but not restricted to, KRP1 and KRP2 (GenBank accessions U94772 and AJ251851, De Veylder et al., *The Plant Cell*, 13: 1653-1667 (2001)) and AtWEE1 (GenBank accession CAD28679, Sorrell et al., Planta, 215(3): 518-522 (2002)).

The phrase "micronutrient content" means the amount of micronutrients, i.e., vitamins A, E, K, tocopherols, tocotrienols, or carotenoids, within a seed expressed on a per weight basis.

The phrase "oil content" means oil level, which may be determined, for example, by low-resolution $^1$H nuclear magnetic resonance (NMR) (Tiwari et al., *JAOCS*, 51:104-109 (1974) or Rubel, *JAOCS*, 71:1057-1062 (1994)) or near infrared transmittance (NIT) spectroscopy (Orman, et al., *JAOCS*, 69(10):1036-1038 (1992); Patrick, et al., *JAOCS*, 74(3):273-276 (1997)).

As used herein, the phrase "oil composition" means the ratio of different fatty acid or oil components within a sample. Such a sample may be a plant or plant part, such as a seed. Such a sample may also be a collection of plant parts.

As used herein, the phrase "percentage content" in a preferred embodiment means the percent by total weight of a particular component, relative to other similar of related components.

As used herein, the phrase "enhanced oil" or "oil enhancing" includes increased oil yield or altered oil composition.

As used herein, the phrase "sucrose phosphorylase" means an enzyme, which catalyzes a reversible conversion of sucrose and inorganic phosphate to alpha-D-glucose-1-phosphate and D-fructose. In may be isolated from many microbial sources, including *Streptococcus mutans, Clostridium pasteurianum, Pseudomonas saccharophila, Pseudomonas putrifaciens, Pullularia pullulans, Acetobacter xylinum, Agrobacterium* sp., and *Leuconostoc mesenteroides* (U.S. Pat. No. 6,235,971).

As used herein, the phrase "starch-enhancing" refers to genes or gene combinations that result in increased levels of polysaccharides, e.g., starch.

As used herein, the term "starch" refers to a carbohydrate polymer occurring in granular form in certain plant species notably cereals, tubers and pulses such as corn, wheat, rice, potato, and soybean. The polymer consists of linked anhydro-a-D-glucose units. It may have either a mainly linear structure (amylase) or a branched structure (amylopectin).

The phrase "protein quality" means the level of one or more essential amino acids, whether free or incorporated in protein, namely histidine, isoleucine, leucine, lysine, methionine, cysteine, phenylalanine, tyrosine, threonine, tryptophan, and valine.

The following examples are included to demonstrate preferred embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

Isolation of the P-Dgat1 and P-Dgat2 Promoters

A genomic DNA library was constructed using genomic DNA isolated from *Arabidopsis thaliana* using a modified genomic DNA isolation protocol described below (Dellaporta et al., (1983) *Plant Molecular Biology Reporter*, 1: 19-21). *Arabidopsis* seedlings were grown in soil or in Petri plates, were harvested, and kept frozen in liquid nitrogen until extraction. The tissue was ground to a fine powder using a mortar and pestle while keeping the tissue frozen with liquid nitrogen. The powdered tissue was transferred to a Waring blender containing 200 mL of cold (0° C.) DNA extraction buffer (350 mM sorbitol; 100 mM Tris; 5 mM EDTA; pH to 7.5 with HCl; sodium bisulfite (3.8 mg/mL) was added just before use), and homogenized at high speed for 30-60 seconds. The homogenate was filtered through a layer of cheesecloth and collected in a centrifuge bottle. The samples were centrifuged at 2500×g for 20 minutes. The supernatant and any loose green material was discarded. The pellet was then resuspended in 1.25 mL of DNA extraction buffer and transferred to a 50 mL polypropylene tube.

Nuclei lysis buffer (1.75 mL containing 200 mM Tris; 50 mM EDTA; 2 M NaCl; 2.0% (w/v) CTAB; pH adjusted to 7.5 with HCl) was then added, followed by addition of 0.6 mL of 5% (w/v) sarkosyl. The tubes were mixed gently, and the samples were incubated at 65° C. for 20 minutes. An equal volume of chloroform:isoamyl alcohol (24:1) was added and the tubes were mixed gently. The tubes were then centrifuged at 2500×g for 15 minutes, and the resulting supernatant was transferred to a clean tube. An equal volume of ice-cold isopropanol was poured onto the sample, and the sample was inverted several times until a precipitate formed. The precipitate was removed from the solution using a glass pipette and residual alcohol removed by allowing the precipitate to air dry for 2-5 minutes. The precipitate was resuspended in 400 µL TE buffer (10 mM Tris-HCl, 1 mM EDTA, pH adjusted to 8.0).

P-Dgat1 Promoter

The P-Dgat1 promoter (SEQ ID NO: 1) was isolated by use of PCR (polymerase chain reaction). The reaction conditions for the PCR reaction followed the manufacturer's protocol (PE Applied Biosystems, Foster City, Calif.). Approximately 100 ng of *Arabidopsis* genomic DNA, prepared as described above, was amplified using 30 nmole each of forward primer (SEQ ID NO: 2) and reverse primer (SEQ ID NO: 3), and 10 micromoles each of dATP, dCTP, dGTP, and TTP, 2.5 units of TaKaRaLA Taq in 1× LA PCR Buffer II (Takara Bio INC, Shiga, Japan). After initial incubation at 94° C. for 1 min., 35 cycles of PCR were performed at 94° C. for 45 seconds, followed by annealing at 60° C. for 45 seconds, 72° C. for 1 minute 15 seconds, followed, by 1 cycle of 72° C. for 7 minutes.

Figure 2:
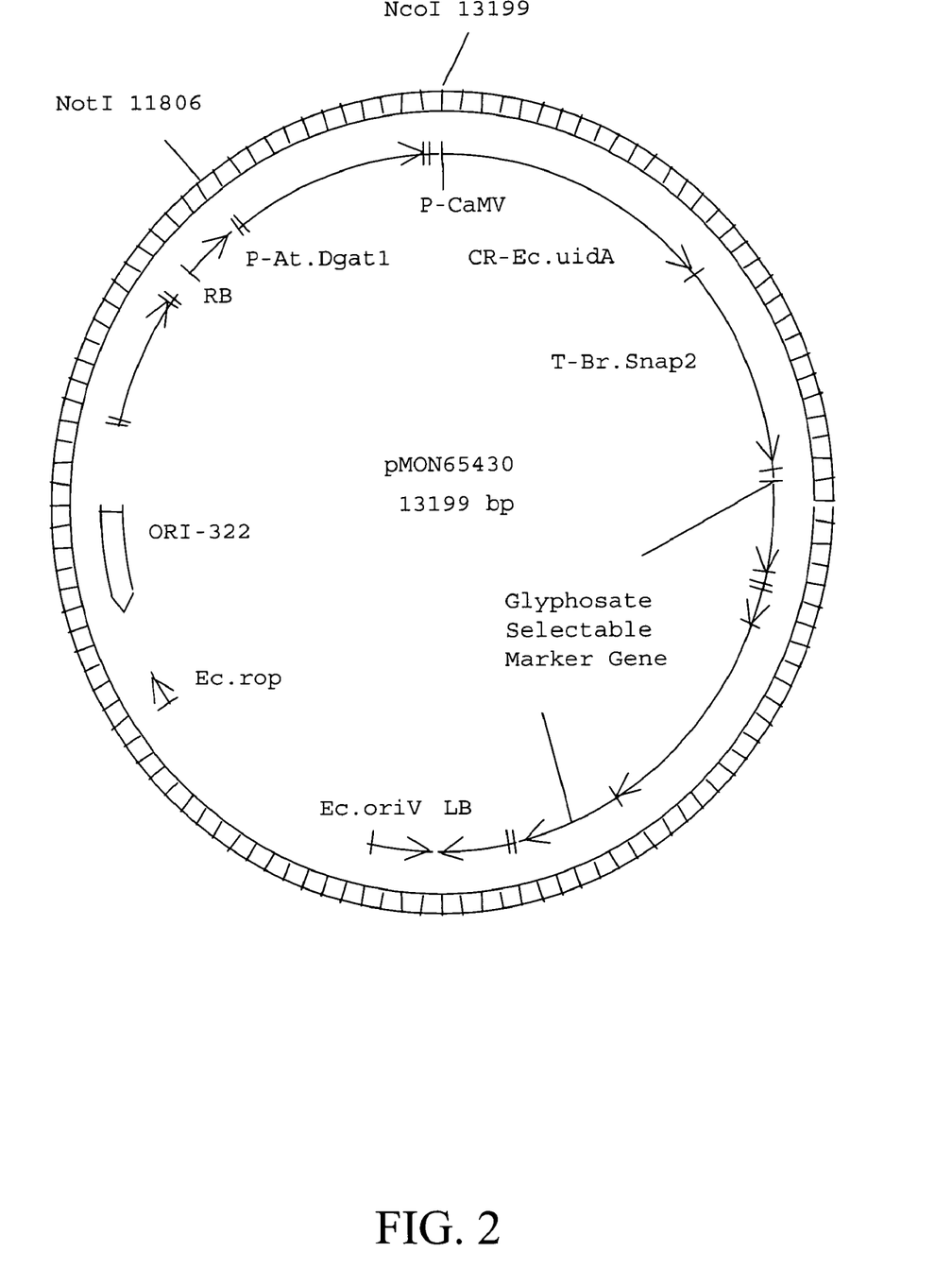
FIG. 2 depicts pMON65430.

The P-Dgat1:*Escherichia coli* glucuronidase (uidA) reporter gene construct was made by isolating a 1250 bp fragment containing the P-Dgat1 promoter by PCR, followed by restriction digestion with PstI and SpeI restriction enzymes. The resulting fragment was ligated into pMON63925, which had also been digested with PstI and SpeI. The resulting plasmid was designated pMON63922. A 1496 bp fragment containing the P-Dgat1 and P-CaMV-70 promoters was removed from pMON63922 by digestion with NcoI and NotI restriction enzymes. The resulting fragment was ligated into pMON65424, which had also been digested with NcoI and NotI. The resulting plasmid, containing P-Dgat1 promoter, in operable linkage with the *E. coli* glucuronidase (uidA) reporter gene and the napin 3' UTR, was subsequently named pMON65430 (FIG. 2). Glyphosate was used as the selectable maker (U.S. Pat. No. 5,633,435). The nucleic acid sequence was determined using standard methodology as set forth by PE Applied Biosystems BigDye terminator v.3.0 (PE Applied Biosystems, Foster City, Calif.) and the integrity of the cloning junctions confirmed. The pMON65430 vector was used in the subsequent transformation of *Arabidopsis* and Canola described in Example 2, below.

P-Dgat2 Promoter

The P-Dgat2 promoter (SEQ ID NO: 4) was isolated by use of PCR (polymerase chain reaction). The reaction conditions for the PCR reaction followed the manufacturer's protocol (PE Applied Biosystems, Foster City, Calif.). Approximately 100 ng of *Arabidopsis* genomic DNA, prepared as described above, was amplified using 30 nmole each of forward primer (SEQ ID NO: 5) and reverse primer (SEQ ID NO: 6), and 10 micromoles each of dATP, dCTP, dGTP and TTP, 2.5 units of AmpliTaq Gold in 1× Opti-Prime™ Buffer 3 (Stratagene, Jolla, Calif. USA). After initial incubation at 95° C. for 10 min., 15 cycles of PCR were performed at 92° C. for 15 seconds, followed by 15 cycles starting at 62° C. and decreasing 0.7° C. per cycle for 20 seconds, 72° C. for 2 minutes, followed by 20 cycles at 92° C. for 15 seconds, 52° C. for 20 seconds, and 72° C. for 2 minutes, followed by 1 cycle of 72° C. for 7 minutes.

The product of the PCR reaction was purified using the QIAquick PCR Purification Kit (Qiagen Inc. Valencia, Calif., USA) according to the manufacturer's instructions and cloned into pCR2.1 Topo (Invitrogen Corp. Carlsbad, Calif., USA) according to the manufacturer's instructions. The resulting plasmid was named pMON65421. The entire sequence of this clone was determined using standard sequencing methodologies as set forth by PE Applied Biosystems (Perkin-Elmer Applied Biosystems Inc., Foster City Calif., USA).

Figure 1:
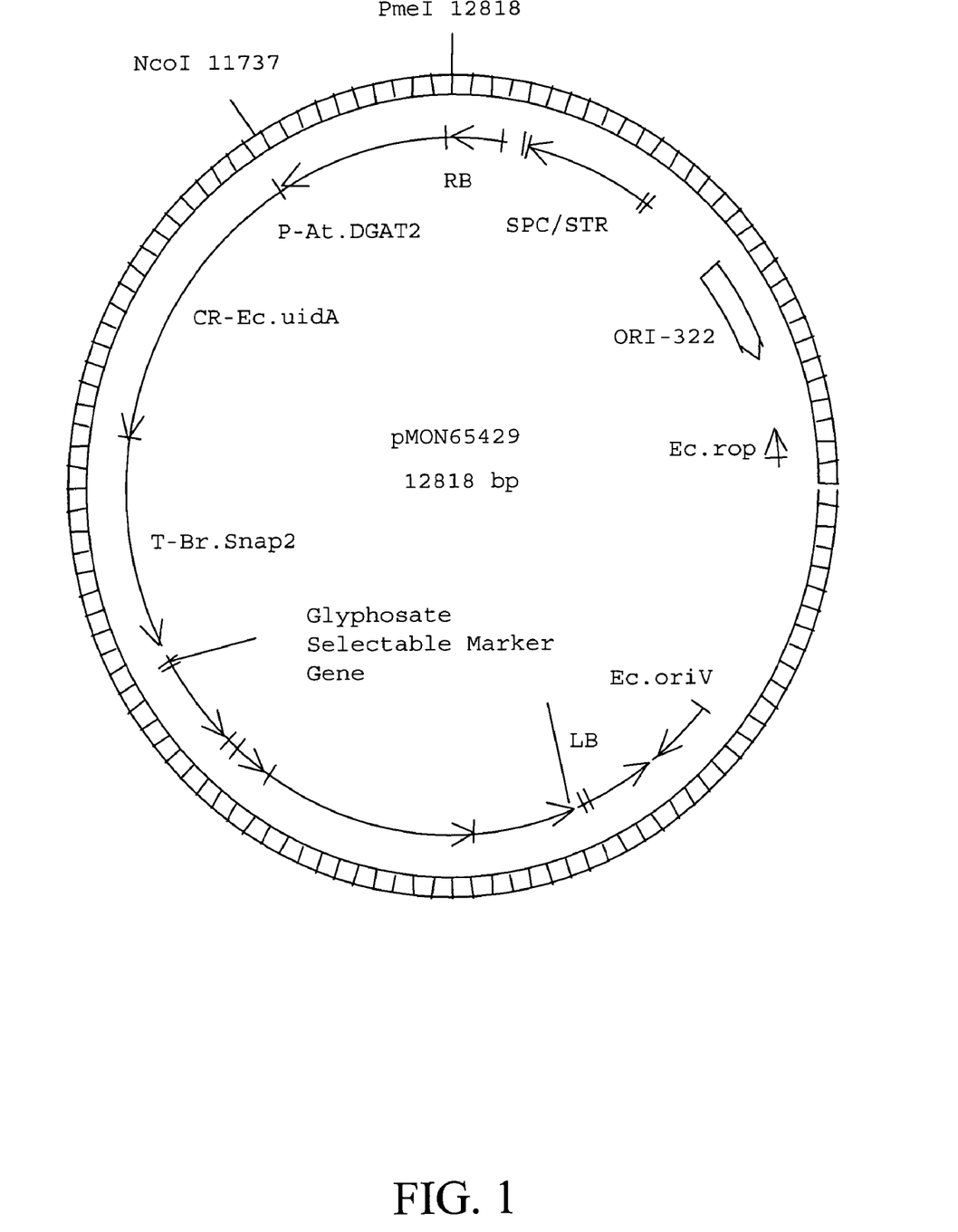
FIG. 1 depicts pMON65429.

The P-Dgat2:*ESCHERICHIA coli* glucuronidase (uidA) reporter gene construct was made by isolating a 1082 bp fragment containing the P-Dgat2 promoter from pMON65421 by restriction digestion with PmeI and NcoI restriction enzymes. The resulting fragment was ligated into pMON65424, which had also been digested with PmeI and NcoI. The resulting plasmid, containing P-Dgat2, in operable linkage with the *E. coli* glucuronidase (uidA) reporter gene and the napin 3' UTR, and was subsequently named pMON65429 (FIG. 1). Glyphosate was used as the selectable maker (U.S. Pat. No. 5,633,435). The nucleic acid sequence was determined, and the integrity of the cloning junctions confirmed, using standard methodology as set forth by the PE Applied Biosystems BigDye terminator v.3.0 protocol (PE Applied Biosystems, Foster City, Calif.). This vector was used in the subsequent transformation of *Arabidopsis* and Canola described in Example 2.

Example 2

*Arabidopsis* and Canola Transformation containing P-Dgat Promoter Constructs The promoters described in Example 1 were operably linked to the marker gene, *Escherichia coli* uidA, in a construct to demonstrate expression in *Arabidopsis* and Canola. Table 2 lists the promoter construct specifics.

TABLE 2

*Arabidopsis* and Canola Transformation Constructs.

| Construct | Promoter | SEQ ID NO | Marker gene | 3' UTR | Fig. |
|---|---|---|---|---|---|
| PMON65429 | P-Dgat2 | 4 | uidA | Napin | 2 |
| PMON65430 | P-Dgat1 | 1 | uidA | Napin | 1 |

*Arabidopsis* plants were grown by sowing seeds onto 4-inch pots containing reverse osmosis water (ROW) saturated MetroMix 200 (The Scotts Company, Columbus, Ohio, USA). The plants were vernalized by placing the pots in a covered flat in a growth chamber at 4-7° C., 8 hours light/day, for 4-7 days. The flats were transferred to a growth chamber at 22° C., 55% relative humidity, and 16 hours light/day at an average intensity of 160-200 μEinstein/s/m². The cover was lifted and slid back 1-inch after germination, and then was removed when the true leaves had formed. The plants were bottom watered as needed with ROW until 2-3 weeks after germination. Plants were then bottom watered as needed with Plantex 15-15-18 solution (Plantex Corporation, Ottawa, Canada) at 50 ppm N2. Pots were thinned so that 1 plant remained per pot at 2-3 weeks after germination. Once the plants began to bolt, the primary inflorescence was trimmed to encourage the growth of axillary bolts.

Transgenic *Arabidopsis thaliana* plants were obtained as described by Bent et al., *Science*, 265:1856-1860 (1994) or Bechtold et al., *C.R. Acad. Sci, Life Sciences*, 316:1194-1199 (1993). Cultures of *Agrobacterium tumefaciens* strain ABI containing either of the transformation vectors pMON65429 or pMON65430 were grown overnight in LB (10% bactotryptone, 5% yeast extract, and 10% NaCl with kanamycin (75 mg/L), chloramphenicol (25 mg/L), and spectinomycin (100 mg/L)). The bacterial culture was centrifuged and resuspended in 5% sucrose+0.05% Silwet-77 solution. The aerial portions of whole *Arabidopsis thaliana* plants (at about 5-7 weeks of age) were immersed in the resulting solution for 2-3 seconds. The excess solution was removed by blotting the plants on paper towels. The dipped plants were placed on their side in a covered flat and transferred to a growth chamber at 19° C. After 16 to 24 hours the dome was removed and the plants were set upright. When plants had reached maturity, water was withheld for 2-7 days prior to seed harvest. Harvested seed was passed through a stainless steel mesh screen (40 holes/inch) to remove debris. The harvested seed was stored in paper coin envelopes at room temperature until analysis.

*Arabidopsis* seeds were surfaced sterilized using a vapor phase sterilization protocol. An open container of seeds was placed in a desiccator with a beaker containing 100 mL of household bleach. Immediately prior to sealing the desiccator, 3 mL concentrated HCl was added to the bleach. The desiccator was sealed and a vacuum applied to allow sterilization by chlorine fumes. Seeds were incubated for several hours. Sterilized seed were sprinkled onto *Arabidopsis* Germination Media containing MS Salts (1×); sucrose (1%); myo-Inositol (100 mg/L); Thiamine-HCl (1 mg/L); Pyridoxine-HCl (500 mg/L); Nicotinic Acid (500 mg/L); MES pH 5.7 (0.05%); and Phytagar (0.7%) supplemented with 50 mg/L glyphosate.

Up to 16 glyphosate resistant seedlings were transplanted to 2¼-inch pots, one seedling per pot, containing MetroMix 200 and were grown under the conditions described above until the initial siliques that had formed began to desiccate. Tissue (rosette leaf, cauline leaf, stem, flowers, floral buds, and developing siliques) was removed from each Ti plant for subsequent histochemical staining. Expression of β-glucuronidase was analyzed in *Arabidopsis thaliana* plants transformed with pMON65430 using histochemical staining. Tissues from transformed and control plants were incubated for approximately 24 hours at 37° C. in a solution containing 50 mM NaPO4 (pH 7.2); 100 μM potassium ferricyanide; 100 μM potassium ferrocyanide, 0.03% Triton X-100; 20% methanol; and 2.5 mg/ml 5-bromo-4-chloro-3-indoyl glucuronic acid (X-gluc). The stained tissue was cleared of chlorophyll by an overnight incubation in 70% ethanol/30% $H_2O$ at 37° C. Stained tissues were photographed immediately or transferred to a solution of 70% ethanol/30% glycerol (v/v) and stored at 4° C. until photographed. For pMON65430, 14 out of 15 events tested had detectable levels of GUS activity in developing seeds.

Example 3

Canola Transformation Containing P-Dgat Constructs

The vectors pMON65429 and pMON65430 were introduced into *Agrobacterium tumefaciens* strain ABI for transformation into *Brassica napus*. Canola plants were transformed using the protocol described by Moloney and Radke in U.S. Pat. No. 5,720,871. Briefly, seeds of *Brassica napus* cv Ebony were planted in 2-inch pots containing Metro Mix 350 (The Scotts Company, Columbus, Ohio, USA). The plants were grown in a growth chamber at 24° C., and a 16/8 hour photoperiod, with light intensity of 400 mEm-2 sec-1 (HID lamps). After 2½ weeks, the plants were transplanted into 6-inch pots and grown in a growth chamber at 15/10° C. day/night temperature, 16/8 hour photoperiod, light intensity of 800 mEm-2 sec-1 (HID lamps).

Four terminal internodes from plants just prior to bolting or in the process of bolting but before flowering were removed and surface sterilized in 70% (v/v) ethanol for 1 minute, 2% (w/v) sodium hypochlorite for 20 minutes and rinsing 3 times with sterile deionized water. Six to seven stem segments were cut into 5 mm discs, maintaining orientation of basal end. The *Agrobacterium* culture used to transform Canola was grown overnight on a rotator shaker at 24° C. in 2 mLs of Luria Broth, LB, (10% bacto-tryptone, 5% yeast extract, and 10% NaCl) containing 50 mg/L kanamycin, 24 mg/L chloramphenicol and 100 mg/L spectinomycin. A 1:10 dilution was made in MS media (Murashige and Skoog, *Physiol. Plant*, 15:473 497, (1962)) giving approximately 9×108 cells per mL. The stem discs (explants) were inoculated with 1.0 mL of *Agrobacterium* and the excess is aspirated from the explants.

The explants were placed basal side down in Petri plates containing media comprising ⅒ MS salts, B5 vitamins (1% inositol; 0.1% thiamine HCl; 0.01% nicotinic acid; 0.01% pyridoxine HCl), 3% sucrose, 0.8% agar, pH 5.7, 1.0 mg/L 6 benzyladenine (BA). The plates were layered with 1.5 mL of media containing MS salts, B5 vitamins, 3% sucrose, pH 5.7, 4.0 mg/L p chlorophenoxyacetic acid, 0.005 mg/L kinetin and covered with sterile filter paper. Following a 2 to 3 day co-culture, the explants were transferred to deep dish Petri plates containing MS salts, B5 vitamins, 3% sucrose, 0.8% agar, pH 5.7, 1 mg/L BA, 500 mg/l carbenicillin, 50 mg/L cefotaxime, and 25 mg/L glyphosate for selection. Seven explants are placed on each plate. After 3 weeks they were transferred to fresh media, 5 explants per plate. The explants were cultured in a growth room at 25° C. under continuous light (Cool White).

The transformed plants were grown in a growth chamber at 22° C., 16/8 hours light-dark cycle with a light intensity of mEm$^{-2}$ sec$^{-1}$ for several weeks before transferring to the greenhouse. Plants were maintained in a greenhouse until harvest. Developing siliques were harvested at various stages after pollination and stored at minus 70° C. Stems, flowers, and leaves were also collected; and stained (as described below) shortly after collection without prior freezing. Mature seed are collected and stored under controlled conditions consisting of about 17° C. and 30% humidity.

Up to 5 siliques were harvested from individual RO plants at several time points after pollination. Siliques were scored with an 18-gauge needle to allow the staining solution to contact the developing seed. The siliques and seed were incubated for approximately 24 hours at 37° C. in a solution containing 50 mM NaPO4 (pH 7.2); 100 mM potassium ferricyanide; 100 mM potassium ferrocyanide, 0.03% Triton X 100; 20% methanol and 2.5 mg/ml 5 bromo 4 chloro 3 indoyl glucuronic acid (X gluc). The stained tissue was cleared of chlorophyll by an overnight incubation in 70% ethanol/30% H$_2$O at 37° C. Stained tissues were photographed immediately or transferred to a solution of 70% ethanol/30% glycerol (v/v) and stored at 4° C. until photographed. Samples were scored positive (+) or negative (−) for blue color.

For plants transformed with pMON65429, 8 out of 10 plants screened had detectable levels of GUS activity in the seed from at least one time point (Table 3). For plants transformed with pMON65430, 7 out of 10 plants screened had detectable levels of GUS activity in the seed from at least one time point (Table 4).

TABLE 3 pMON65429 Expression in Developing Canola Seed

| Construct | Event | Days After Pollination | | | | | | | | |
|---|---|---|---|---|---|---|---|---|---|---|
| | | 3 | 6 | 9 | 12 | 15 | 20 | 25 | 30 | 35 | 40 |
| PMON65429 | BN_G1151 | − | + | + | + | + | + | + | + | + | + |
| PMON65429 | BN_G1152 | − | − | − | − | − | − | + | + | + | + |
| PMON65429 | BN_G1153 | + | + | + | + | + | + | + | + | + | + |
| PMON65429 | BN_G1154 | − | − | − | − | + | + | + | + | + | + |
| PMON65429 | BN_G1155 | − | + | + | + | + | + | + | + | + | + |
| PMON65429 | BN_G1156 | − | − | + | + | + | − | + | + | + | + |
| PMON65429 | BN_G1188 | − | − | − | − | − | − | − | − | − | − |
| PMON65429 | BN_G1189 | + | + | + | + | + | + | + | + | + | + |
| PMON65429 | BN_G1190 | − | + | + | + | + | + | + | + | + | + |
| PMON65429 | BN_G1191 | − | − | − | − | − | + | + | + | + | + |
| SP30052 | Control | − | − | − | − | − | − | − | − | − | − |

TABLE 4 pMON65430 Expression in Developing Canola Seed

| Construct | Event | Days After Pollination | | | | | | | | |
|---|---|---|---|---|---|---|---|---|---|---|
| | | 3 | 6 | 9 | 12 | 15 | 20 | 25 | 30 | 35 | 40 |
| PMON65430 | BN_G2059 | + | − | − | − | + | − | − | − | − | + |
| PMON65430 | BN_G2060 | − | − | − | − | − | − | − | − | − | + |
| PMON65430 | BN_G2061 | + | − | + | + | − | − | + | − | − | − |
| PMON65430 | BN_G2063 | + | + | + | + | + | − | − | − | − | − |
| PMON65430 | BN_G2107 | − | − | − | − | − | − | − | − | − | − |
| PMON65430 | BN_G2108 | − | − | − | − | − | − | − | − | − | − |
| PMON65430 | BN_G2151 | − | − | − | − | − | − | − | − | − | − |

TABLE 4-continued pMON65430 Expression in Developing Canola Seed

| Construct | Event | Days After Pollination | | | | | | | | | |
|---|---|---|---|---|---|---|---|---|---|---|---|
| | | 3 | 6 | 9 | 12 | 15 | 20 | 25 | 30 | 35 | 40 |
| PMON65430 | BN__G2320 | + | + | + | − | + | + | − | − | − | − |
| PMON65430 | BN__G2321 | + | + | + | − | + | − | − | − | − | − |
| PMON65430 | BN__G2349 | − | − | − | − | + | − | − | − | − | − |
| PMON65430 | Control | − | − | − | − | − | − | − | − | − | − |

Having illustrated and described the principles of the present invention, it should be apparent to persons skilled in the art that the invention can be modified in arrangement and detail without departing from such principles. We claim all modifications that are within the spirit and scope of the appended claims. All publications and published patent documents cited in this specification are incorporated herein by reference to the same extent as if each individual publication or patent application is specifically and individually indicated to be incorporated by reference.

What is claimed is:

1. A promoter comprising a polynucleotide molecule comprising at least 95% sequence identity to the polynucleotide sequence of SEQ ID NO:4 capable of regulating transcription of an operably linked transcribable polynucleotide molecule, wherein said promoter is operably linked to a heterologous transcribable polynucleotide molecule.

2. The promoter of claim 1, wherein said promoter comprises a polynucleotide molecule comprising at least about 98% sequence identity to the polynucleotide sequence of SEQ ID NO:4.

3. The promoter of claim 1, wherein said promoter comprises a polynucleotide molecule comprising at least about 99% sequence identity to the polynucleotide sequence of SEQ ID NO:4.

4. The promoter of claim 1, wherein said transcribable polynucleotide molecule is a gene of agronomic interest.

5. The promoter of claim 4, wherein the gene of agronomic interest is an oil enhancing gene selected from the group consisting of Diacylglycerol Acyltransferase, Phosphatidic Acid Phosphatase, and Leucoanthocyanidin Dioxygenase.

6. The promoter of claim 4, wherein the gene of agronomic interest is a starch enhancing gene comprising Sucrose Phosphorylase.

7. The promoter of claim 1, wherein said transcribable polynucleotide molecule is a marker gene.

8. A transgenic plant or part thereof stably transformed with the promoter of claim 1.

9. The transgenic plant or part thereof of claim 8, wherein said plant is a dicotyledonous plant selected from the group consisting of tobacco, tomato, potato, soybean, cotton, canola, sunflower, and alfalfa.

10. The transgenic plant or part thereof of claim 8, wherein said transcribable polynucleotide molecule confers altered cell proliferation in the embryo, aleurone, or both to said transgenic plant.

11. The transgenic plant or part thereof of claim 8, wherein said transcribable polynucleotide molecule confers altered oil content in the embryo, aleurone, or both to said transgenic plant.

12. The transgenic plant or part thereof of claim 8, wherein said transcribable polynucleotide molecule confers altered protein quality in the embryo, aleurone, or both to said transgenic plant.

13. The transgenic plant or part thereof of claim 8, wherein said transcribable polynucleotide molecule confers altered micronutrient content to said transgenic plant.

14. A seed transformed with the promoter of claim 1.

15. A cell transformed with the promoter of claim 1.

16. A method of making a vegetable oil, comprising the steps of:
a) obtaining the transgenic seed of claim 14; and
b) extracting oil from the seed.

17. A method of making a vegetable protein, comprising the steps of:
a) obtaining the transgenic seed of claim 14; and
b) extracting the protein from the seed.

18. The method of claim 16, wherein the promoter is operably linked to a transcribable polynucleotide molecule conferring altered protein content.

19. A method of making food or feed comprising:
a) obtaining the plant or part thereof of claim 8; and
b) preparing food or feed from the plant or part thereof.

* * * * *

```
                       SEQUENCE LISTING

<160> NUMBER OF SEQ ID NOS: 6

<210> SEQ ID NO 1
<211> LENGTH: 1262
<212> TYPE: DNA
<213> ORGANISM: Arabidopsis thaliana

<400> SEQUENCE: 1
tgaatcaaac tataagtcgg attgaatcaa actataagtc ggatgagtat taatttccat     60
tatgtttcta tactttacaa accggaaaat agatattata gataccaaaa aagtagattt    120
gtgtatatta ttagaagatt tggaatttca tcattatcag gatctaaagt acttccctaa    180
ttaaatcatg tcggttgaaa aagctcaatg aatgtttgaa atttggaaag tttattaaat    240
tcggatcttt ttttttttgtt tgtcgtccca aacattttta ttttattaca aataatcaac    300
ttatccttac tactaaatca tttcatatct ttgataccaa caaatcattt catattctat    360
tttgatgttt aagaaaacac tatttaccag ttacaaaata ttataaggat tgttgtttag    420
aaaaaaaagt acaagttgaa ttcttttttgt caaatataaa attgactttt taatatataa    480
ttgacttatt gaacatgatt acagaattaa tcatctacaa aactttccaa gtttataata    540
aatacatttc aaagactatt agttcttctt aaaatatttc taaagtgat caaagactac    600 cacatataat tcagaaaaag tagaagttga tttcttttttg tcaaataaat aattgactta    660
aaatagtttg gaaagccatt gaacttgatt atagaattga taatgtacat aaaaaaattc    720
caagtttata ataaatacat ttttcaaatg ctatatcagt tcttcttaaa atatttcact    780
aaaaaaacac tcaaatatag aataaattta ttgaataaca taccaactgt aaaacagaat    840
ttgacaaaaa aaaaaaaaaa atgaaatgaa gatgaagaca aaaataaatc accagaggat    900
cttatgcaaa aaaatatatg aatacacaat aaaccatatt gatattttta aaataaaata    960
aaaacagaaa aatatcccaa caccgctttt caattaaaaa tcttccgtca ccattgttgt   1020
catcttcctc tctcgtgaat cctttttcct ttcttcttct tcttctcttc agagaaaact   1080
ttgcttctct ttctataagg aaccagacac gaatcccatt cccaccgatt tcttagcttc   1140
ttccttcaat ccgctctttc cctctccatt agattctgtt tcctctttca atttcttctg   1200
catgcttctc gattctctct gacgcctctt ttctcccgac gctgttcgtc aaacgctttt   1260
cg                                                                  1262

<210> SEQ ID NO 2
```

```
<211> LENGTH: 60
<212> TYPE: DNA
<213> ORGANISM: Artificial
<220> FEATURE:
<223> OTHER INFORMATION: Synthetic primer

<400> SEQUENCE: 2
ggggacaagt ttgtacaaaa aagcaggcta ctgcagtgaa tcaaactata agtcggattg    60

<210> SEQ ID NO 3
<211> LENGTH: 56
<212> TYPE: DNA
<213> ORGANISM: Artificial
<220> FEATURE:
<223> OTHER INFORMATION: Synthetic primer

<400> SEQUENCE: 3
ggggaccact ttgtacaaga aagctgggta actagtcgaa aagcgtttga cgaaac         56

<210> SEQ ID NO 4
<211> LENGTH: 1073
<212> TYPE: DNA
<213> ORGANISM: Arabidopsis thaliana

<400> SEQUENCE: 4
tcttactgga atccccactt ctgtgagttc cttgtctctc tcttttcgtt tttatccatt    60
tgatctgtat cagctgaaaa aatggttttt ttgcgttcag gtgttcctat ggttcaaatc   120
cgttgaagct gctaataagg aagctcaaga acaagataaa agagatggct ttctttaaaa   180
tccttttgtg tgattctgca actcatacag tgatgattgt tgtctccaca tatactttga   240
atataattct gcatttacaa aggagcttgc ttctgttcac tgtttatcac ccgctagatt   300
ttgtttgtaa tttcaacaat atgccatgtt ccaacgagta agtgcctgaa attcgatgat   360
cagctgtcct ctctttatt tgcccctgtg aaagatatga atccacaaag aattcgatat    420
gccatcctgc ggtttgaatg tctgaagctg atggtaatgt caccatttgt tcaatgagtt   480
gatattcaga tcaacaattt gttctggaaa gacattgcct gctttcattt gttggtagga   540
gattggagtc aaaatatcag ttgaaagtta attccttggc gcttgaagat tgtgcttgag   600
cagaggctgt ttccggggaa tgatcacata caaaatcatg tgtttaattg gtttgtctat   660
gaatgtattt tcagttgaat ataagtcgag ctctaggctc aatttagcag ccagaagtga   720
tacctttgga aggaagatat ctaattggta agcaaaaact gttaaaagca cttacataca   780
gataaatcaa tgtccttttgg cccaatatta gctttaacaa aggcttaacc ttttgaaaac   840
tccagttagg caataattat tacgggtcaa atgacaaaga atgaaccttg tcgggctctt   900
taaagatggg ttgttgtata aaaagttggg tagttaaaag attggttatt tgggctctgc   960
actcaagtga gagagaagat agatagatct gagtagaatc ttcgattcat tattcgttgt  1020
cgtcgttcat ctgtgagaag cggacaaacc aaagaatcca ccggagctgc cac          1073

<210> SEQ ID NO 5
<211> LENGTH: 29
<212> TYPE: DNA
<213> ORGANISM: Artificial
<220> FEATURE:
<223> OTHER INFORMATION: Synthetic primer

<400> SEQUENCE: 5
gtttaaactc ttactggaat ccccacttc                                       29

<210> SEQ ID NO 6
```

```
<211> LENGTH: 29
<212> TYPE: DNA
<213> ORGANISM: Artificial
<220> FEATURE:
<223> OTHER INFORMATION: Synthetic primer

<400> SEQUENCE: 6
ccacccatgg tggcagctcc ggtggattc                                           29
```